United States Patent
Provonchee

(10) Patent No.: US 12,297,298 B2
(45) Date of Patent: May 13, 2025

(54) AGAROID STRUCTURES AND RELATED METHODS OF USE AND MANUFACTURE

(71) Applicant: Advance Aesthetic Technologies, Inc., Brookline, MA (US)

(72) Inventor: Richard Provonchee, Cushing, ME (US)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 359 days.

(21) Appl. No.: 16/613,342

(22) PCT Filed: May 16, 2018

(86) PCT No.: PCT/US2018/032911
§ 371 (c)(1),
(2) Date: Nov. 13, 2019

(87) PCT Pub. No.: WO2018/213408
PCT Pub. Date: Nov. 22, 2018

(65) Prior Publication Data
US 2020/0181293 A1    Jun. 11, 2020

Related U.S. Application Data

(60) Provisional application No. 62/507,302, filed on May 17, 2017.

(51) Int. Cl.
| C08B 37/00 | (2006.01) |
| A61L 27/20 | (2006.01) |
| A61L 27/36 | (2006.01) |
| A61L 27/54 | (2006.01) |
| A61L 27/56 | (2006.01) |

(52) U.S. Cl.
CPC .......... *C08B 37/0039* (2013.01); *A61L 27/20* (2013.01); *A61L 27/3687* (2013.01); *A61L 27/54* (2013.01); *A61L 27/56* (2013.01); *C08B 37/0003* (2013.01); *A61L 2300/402* (2013.01); *A61L 2300/404* (2013.01); *A61L 2300/418* (2013.01)

(58) Field of Classification Search
CPC .......... A61L 27/54; A61L 27/20; A61L 27/52; A61L 27/56; A61L 27/3687; A61L 2300/402; A61L 2300/418; A61L 2400/12; A61L 2400/06; C08B 37/0039; C08B 37/0003; C08L 5/12
USPC ....................................................... 536/124
See application file for complete search history.

(56) References Cited

U.S. PATENT DOCUMENTS

| 5,670,636 A | 9/1997 | Provonchee |
| 7,309,232 B2 | 12/2007 | Rutherford et al. |

FOREIGN PATENT DOCUMENTS

| CA | 2632630 | 6/2007 |
| JP | 5-502056 | 4/1993 |
| WO | 2003072155 A1 | 9/2003 |
| WO | WO 2007/070660 A2 * | 6/2007 |

OTHER PUBLICATIONS

Saaiq et al, World Journal of Clinical Cases, 2014, 2(10), 507-514.*
Fernandez-Cossio et al., "Biocompatibility of agarose gel as a dermal filler: histologic evaluation of subcutaneous implants", PubChem Compound, MedGen, Oct. 2007, vol. 120, Issue 5, pp. 1161-1169, Abstract only, 2 pages.
Kolanthai et al., "Effect of solvent; enhancing the wettability and engineering the porous structure of a calcium phosphate/agarose composite for drug delivery", Royal Society of Chemistry, vol. 5, Issue 24, Jan. 1, 2015, pp. 18301-18311, 11 pages.
Chiu, YC et al, "Generation of Porous Poly(Ethylene Glycol)Hydrogels by Salt Leaching" Tissue Engineering: Part C. vol. 16, No. 5, 2010 pp. 905-912, p. 906, col. 1, paragraph 3, p. 906, col. 2, paragraph 3.
Varshosaz et al., "Preparation, Optimization, and Screening of the Effect of Processing Variables on Agar Nanospheres Loaded with Bupropion HCl by a D-Optimal Design", Hindawi Publishing Corporation, BioMed Research International, May 19, 2015, vol. 2015, Article ID 571816, 14 pages.
Hutmacher et al., "An introduction to biodegradable materials for tissue engineering applications", Ann Acad Med Singap. 2001, vol. 30, Issue 2, pp. 183-191, 9 pages.
Zucca et al., "Agarose and Its Derivatives as Supports for Enzyme Immobilization", Molecules, 2016, vol. 21, Issue 11, 25 pages.
Annabi, "Controlling the porosity and microarchitecture of hydrogels for tissue engineering", Tissue Eng Part B Rev., 2010, vol. 16, Issue 4, 14 pages.
Bao et al. "Agar/collagen membrane as skin dressing for wounds." Biomed. Mater. 3.4(2008): 1-7.

(Continued)

*Primary Examiner* — Ganapathy Krishnan
(74) *Attorney, Agent, or Firm* — WOMBLE BOND DICKINSON; Deborah M. Vernon; Ricardo Joseph

(57) ABSTRACT

Agaroid structures in the form of an agaroid matrix, a sintered agaroid, or an agaroid mat are disclosed which may, in some embodiments, include a chemically crosslinked agaroid, a derivatized agaroid, and/or an agaroid coupled with one or more ligands. The agaroid structures may be formed by precipitation from a glycol solution, in some cases, and may be converted to be insoluble in water below 40C. In another aspect, methods of treating a condition of a mammal are disclosed, which include contacting an area of a mammalian body with a composition having an agaroid structure with or without one or more beneficial agents. In yet another aspect, the present disclosure provides methods of filling or bulking tissue in a mammalian body by implanting a converted agaroid composition into the mammalian body, which may include converted agaroid microbeads and/or converted agaroid particles.

11 Claims, 3 Drawing Sheets

(56) References Cited

OTHER PUBLICATIONS

Dekosky et al. "Hierarchically Designed Agarose and Poly(Ethylene Glycol) Interpenetrating Network Hydrogels for Cartilage Tissue Engineering." Tissue Eng.: Part C. 16.6(201): 1533-1542.

* cited by examiner

AGAROID STRUCTURES AND RELATED METHODS OF USE AND MANUFACTURE

CROSS REFERENCE TO RELATED APPLICATION

This application claims priority from U.S. Provisional Application Ser. No. 62/507,302, titled "Agaroid Structures and Methods of Use Thereof" filed May 17, 2017, the contents of which is incorporated by reference herein.

BACKGROUND

Agarose is a linear polysaccharide polymer made up of repeating units of agarobiose, which is a disaccharide formed of D-galactose and 3,6-anhydro-L-galactopyranose. Agarose is one of the two principal components of agar and is purified from agar by removing agar's other component, agaropectin. Agarose is frequently used in molecular biology for the separation of large molecules, especially DNA, by electrophoresis.

SUMMARY

In certain embodiments, this disclosure relates to agaroid structures, including agaroid matrices, mats, fibers, beads, spheres, microbeads, and microparticles. As compared to conventional agaroids, the disclosed agaroid structures may be formed using unique techniques that produce monolithic structures having interconnected pores throughout. The porous nature of some of the disclosed agaroids allows them to be somewhat sponge-like, readily absorbing water when present and releasing the water absorbed when squeezed. The disclosed agaroid structures may also, in some embodiments, be chemically cross-linked, sintered, and/or contain one or more pore-forming agents. The disclosed agaroid structures may adopt various shapes selected for the desired application.

In some embodiments, the disclosed agaroids may include one or more beneficial agents, which may be selected based on the intended use of the agaroid. Beneficial agents that may be used in connection with the agaroid structures include but are not limited to: imaging contrast agents, radiopaque agents, pigmentation agents, anti-pigmentation agents, moisturizing agents, tensioning agents, anti-acne agents, antioxidants, anti-itch agents, anti-cellulite agents, anti-scarring agents, anti-inflammatory agents, analgesics, anesthetics, and active pharmaceuticals. If present, the beneficial agent(s) included in the agaroid structures may be configured for quick-release or time-elapsed release.

Additionally, the present disclosure also relates to methods of manufacturing the disclosed agaroids. Example methods of manufacture include but are not limited to preparing a solution comprising water and glycol, adding agarose and heating the solution to form an agarose mixture, cooling the mixture to form an agarose precipitate (alternatively referred to herein as an "agaroid structure"), and removing the precipitate from the mixture. After formation of the agaroid structure, the structure may be further processed by converting the agaroid structure to have dissolution properties exhibited by a conventional agaroid. Additional optional processing of the disclosed agaroid structures may include chemically cross-linking the agaroid structure and/or sintering the agaroid structure.

In another aspect, the present disclosure relates to methods of using the disclosed agaroid structures in or on a mammalian body. The disclosed agaroid structures may be used, for example, to treat a wound or skin injury in a subject. In some particular embodiments, an agaroid structure may be used to treat a site of active bleeding in a patient. In some embodiments, the disclosed agaroid structures may be used to stabilize a bone supplement at a bone void or bone graft site, by, for example, delivering to the bone void or bone graft site a composition comprising an agaroid structure comprising a bone supplement. In other embodiments, an agaroid structure may be used to fill and/or bulk soft tissue in a subject. In further aspects, the disclosure provides methods of creating masses in tissue or body voids in a subject, by, for example, administering to the tissue or body void a formulation comprising an agaroid structure as disclosed herein.

In some embodiments, methods of delivering one or more beneficial agents in or on a mammalian body are disclosed, which include incorporating the beneficial agent(s) into an agaroid matrix and applying said agaroid matrix in or on the mammalian body. In select embodiments, the disclosed methods further include imbibing the one or more beneficial agents into an agaroid matrix and applying said agaroid matrix in or on the mammalian body. Beneficial agents that may be used in connection with the agaroid structures may be of any type described herein, including active pharmaceuticals, or any other type of therapeutic or cosmetic agent useful to a mammalian patient.

DETAILED DESCRIPTION

Various agaroid structures are disclosed herein, including formulations comprising the disclosed agaroid structures. Example method of production are also described, along with possible methods of use for application on or in a mammalian body. As will be understood, some exemplary formulations include one or more beneficial agents dispersed in an agaroid structure, which may provide therapeutic benefit when the formulation is applied to treat a mammal.

Exemplary Agaroid Structures and Formulations

Figure 1A:
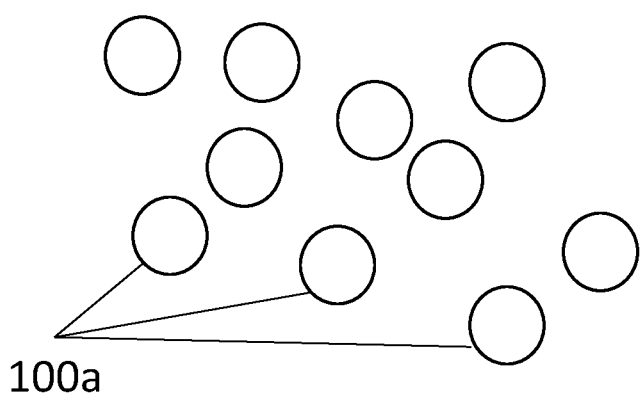
FIGS. 1A-1C show exemplary agaroid structures, in accordance with some embodiments of the subject disclosure.
Figure 1B:
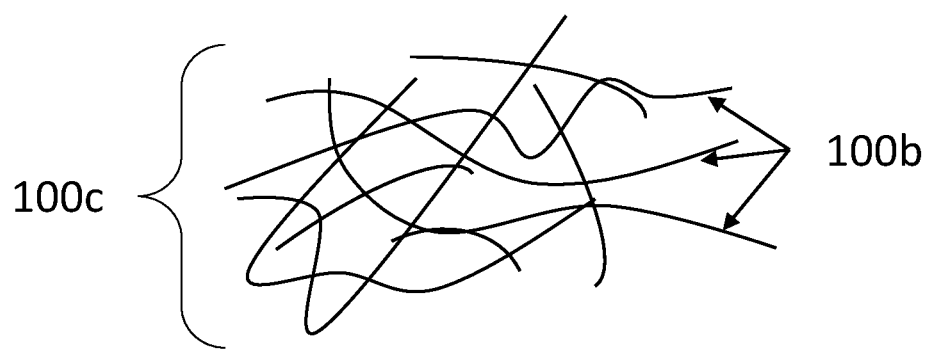
Figure 1C:
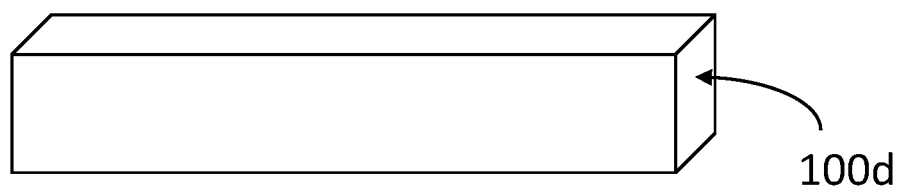

FIGS. 1A-1C show a few exemplary agaroid structures. While the particular agaroid structures shown in FIGS. 1A-1C are identified using reference numerals 100a-100d, these and other agaroid structures are referred to herein generally as "agaroid structure(s) 100." FIG. 1A, for example, illustrates a plurality of agaroid beads 100a. Agaroid beads 100a may be approximately spherical and may, in some embodiments, have a diameter of less than 10 mm, 5 mm, 2 mm, 1 mm, or 0.5 mm. In some embodiments, agaroid beads 100a may be microbeads and may have a diameter of less than 100 microns, 50 microns, 40 microns, 30 microns, 25 microns, 20 microns, 10 microns, or 1 micron. In some embodiments, agaroid beads 100a may have a substantially smooth surface while in other embodiments, agaroid beads 100a may have a rough surface. Agaroid beads 100a may be porous and, in some embodiments, may be formed of a monolithic agaroid material with an interconnected network of pores formed therein.

FIG. 1B illustrates exemplary agaroid fibers 100b. As shown in FIG. 1B, together, agaroid fibers 100b form agaroid mat 100c. Agaroid fibers 100b may be hollow or non-hollow. In some embodiments, agaroid fibers 100b may be porous. As described below in detail, agaroid fibers 100b may be sintered together (for example, through controlled exposure to water before or during the converting process) to fuse fibers 100b together to form an agaroid mat 100c.

FIG. 1C illustrates an exemplary agaroid matrix 100d. Although not illustrated in FIG. 1C, agaroid matrix 100d may include a plurality of pores throughout its structure. In some embodiments, the pores of agaroid matrix 100d may be between 1 and 20 microns in diameter. In select embodiments, agaroid matrix 100d may be a monolithic agaroid material with a plurality of interconnected pores formed throughout the structure. The porous and sponge-like nature of an agaroid matrix may enable it to readily absorb bodily fluids. In some embodiments, when agaroid matrix is dried, it will collapse upon itself to some degree and may not expand to 100% of original size when exposed to an aqueous environment. The degree of dryness and addition of humectants and the like may have an impact on the percent re-expansion of an agaroid matrix.

Any type of suitable agaroid(s) may be used to form the disclosed agaroid structures. For example, the presently disclosed agaroid structures may include, in some embodiments, one or more crude, purified, or modified agars or agaroses. For example, in certain embodiments, the agaroid may be selected from agar, agarose, purified agarose, and derivatized agarose. The agaroids may also be used as mixtures with other compatible polymers and additives such as carrageenan, chitosan, alginate, gelatin, hyaluronic acid, and/or collagen. In select embodiments, the agaroid used to form the agaroid structure is selected from the group consisting of: agar, agarose, derivatized agar, and derivatized agarose. In some embodiments, derivatized carboxy methyl agarose may be used to form the disclosed agaroid structures. In certain embodiments, the agaroid is Gracilaria-derived agarose. Gracilaria-derived agarose has a higher methoxy content than agarose derived from other sources (e.g., Gelidium). In certain embodiments, a combination of two or more agaroids may be used to form an agaroid structure. Agaroids from other seaweeds, for example, Pterocladia or Gelidiella may also be used.

If desired, one or more beneficial agents may be incorporated into the agaroid structures. Example beneficial agents that may be incorporated into the disclosed agaroid structures include but are not limited to: imaging contrast agents, radiopaque agents, pigmentation agents, anti-pigmentation agents, moisturizing agents, tensioning agents, anti-acne agents, antioxidants, anti-itch agents, anti-cellulite agents, anti-scarring agents, anti-inflammatory agents, analgesics, anesthetics, and active pharmaceuticals. In some embodiments, one or more beneficial agents may be present in a weight percent of at least 1%, 5%, or 10% relative to the total weight of agaroid.

In some embodiments, one or more additives may also be present in agaroid structure 100. For example, depending on the method of formation or additional processing used, the disclosed agaroid structures 100 may include one or more of the following additives: pore-forming agents, chemical cross-linking agents, and/or ligands. Example pore-forming agents that may be present in the agaroid structures 100 include but are not limited to sodium chloride. Example chemical cross-linking agents that may be present in the agaroid structures 100 include epichlorohydrin, 2,3-dibromopropanol, bis-epoxides, divinyl sulfone, and bifunctional isocyanates. Example ligands that may be present in the disclosed agaroid structures include monodentate and polydentate (e.g., bidentate and tridentate) ligands. Numerous configurations and variations will be apparent to those skilled in the art upon consideration of the subject disclosure.

Methods of Manufacture

Figure 2:
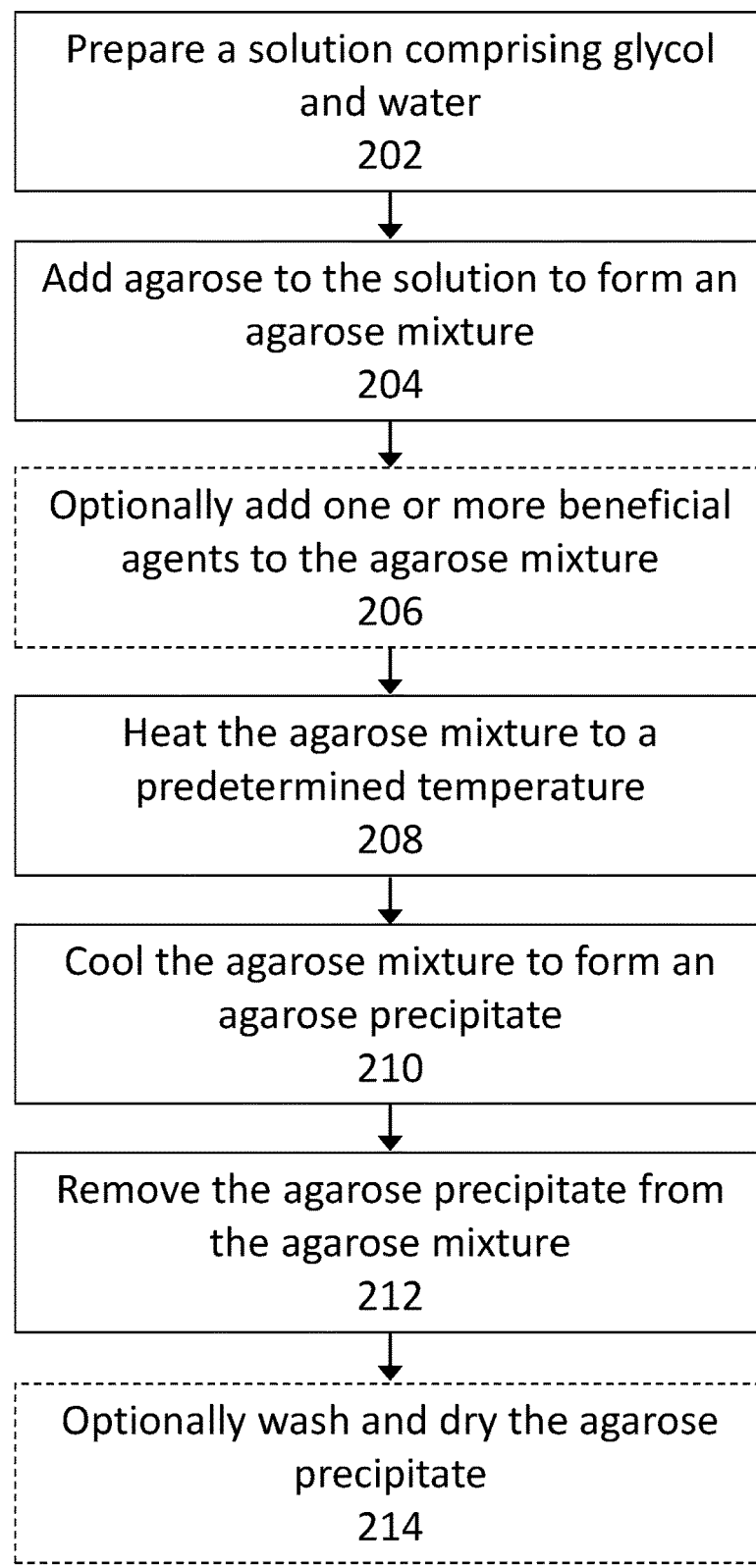
FIG. 2 shows an exemplary method of forming agaroid structures, in accordance with some embodiments of the present disclosure.

The disclosed agaroid structures may be produced using any suitable technique. FIG. 2 illustrates an exemplary method 200 of producing an agaroid structure 100. As shown in FIG. 2, method 200 includes preparing 202 a solution comprising glycol and water. Example glycols that may be used to prepare 202 the solution include one or more $C_1$-$C_4$ alkylene glycols, including, but not limited to: ethylene glycol, diethylene glycol, triethylene glycol, trimethylene glycol, propylene glycol, and butylene glycol (1,2-butanediol). It is well recognized that polyethylene glycols, such as triethylene glycol, contain other glycols (e.g. ethylene glycol, diethylene glycol and the like) and may be used to prepare 202 the solution comprising water and glycol. Water and glycol may be present in any suitable weight ratio in the solution, such as, for example, 1:99-30:70 water to glycol, 5:95-25:75 water to glycol, 10:90-20:80 water to glycol, or approximately 15:85 water to glycol.

Method 200 continues with adding 204 agarose to the solution to form an agarose mixture. The amount of agarose added 204 to the solution may be between 1% and 25%, based on the total weight of the solution. In some embodiments, the agarose may be added 204 to the solution while the solution is at room temperature or below. For example, in some embodiments, the solution of glycol and water may be less than 30° C., 25° C., 20° C., 15° C., or 10° C. while the agarose is added 204.

Method 200 continues with optionally adding 206 one or more beneficial agents to the agarose mixture. Example beneficial agents that may be added 206 to the agarose mixture include but are not limited to: imaging contrast agents, radiopaque agents, pigmentation agents, anti-pigmentation agents, moisturizing agents, tensioning agents, anti-acne agents, antioxidants, anti-itch agents, anti-cellulite agents, anti-scarring agents, anti-inflammatory agents, analgesics, anesthetics, and active pharmaceuticals.

Method 200 continues with heating 208 the agarose mixture to a predetermined temperature. In some embodiments, the agarose mixture may be heated 208 to at least 70° C., 90° C., 100° C., 110° C., 120° C., 130° C., 140° C., or 150° C. In some embodiments, the agarose mixture is heated 208 to a temperature between 100° C. and 120° C. The agarose mixture may be heated until all the agarose present is dissolved. Any suitable heating technique may be used to heat 208 the agarose mixture, including exposure to a hot plate or another type of heating device.

Method 200 continues with cooling 210 the agarose mixture to form an agarose precipitate. Cooling 210 may be conducted over a predetermined period of time (e.g., between 5 minutes and 5 hours, 10 minutes and 4 hours, 15 minutes and 3 hours, and 30 minutes and 2 hours). In some embodiments, slow cooling of the agarose mixture may result in an agaroid structure having a relatively smooth surface, while faster cooling may result in an agaroid structure having a relatively rough surface. The agarose mixture may be cooled to any suitable temperature to cause precipitation of the agarose. In some embodiments, for example, the agarose may be cooled to approximately room temperature, which may cause agarose precipitation.

During cooling 210, the agarose mixture may optionally be stirred. In some such embodiments, the agarose mixture may be gently, moderately, or rapidly stirred during cooling 210. Stirring of the agarose mixture may be performed manually or automatically with a stirrer propelled by a device (e.g., a magnet). In some cases, the degree of agitation to which the agarose mixture is subjected to while cooling may affect the resulting agaroid structure.

In some embodiments, the manner in which agarose mixture is cooled 210 may determine the resulting agaroid structure. For example, in some embodiments, an agaroid matrix may be formed as a thread like structure, for example, by extruding the hot agarose mixture into a cool non-aqueous liquid, allowing it to precipitate with little or no agitation. In another example, the hot agarose mixture may be pumped through tubing that has a chilled section thereby precipitating the agaroid in a rod shape approximating the internal diameter of the tubing. In this manner, an agaroid matrix can be formed as a tube similar to the way plastic tubing is formed. In other embodiments, agaroid matrix can be formed into beads by, for instance, dropping hot agarose mixture into a cool non-aqueous liquid (e.g., isopropyl alcohol) and allowing the beads to cool without agitation. Very small agaroid matrix beads can be formed by, for example, spraying fine droplets of hot agarose mixture into a cooling tower and allowing them to precipitate. To form an agaroid mat, hot agarose mixture may be run through a spinneret and onto a surface under conditions that allow the agaroid in the glycol solution to cool and precipitate prior to reaching or just as it reaches the target surface, thereby creating a non-woven mat structure. In other embodiments, the agarose matrix can be cast by, for instance, pouring the hot agarose mixture into a mold and allowing the agaroid to precipitate in a quiescent state, thereby allowing the agaroid matrix to have the form of the mold. Numerous possibilities and variations are possible and contemplated.

Method 200 continues with removing 212 the agarose precipitate from the agarose mixture. The agarose precipitate may be removed 212 using filtration techniques, centrifuging, or another suitable separation method. Method 200 continues with optionally washing 214 and drying the agarose precipitate. If desired, the agarose precipitate may be washed 214 with isopropanol alcohol and dried (e.g., in a hot-air oven).

Due to the nature of the agarose precipitation process (described in method 200 of FIG. 2), an agaroid having unique structural properties may be produced. Specifically, an agaroid structure made from essentially solid agaroid with an interconnected pore network may be formed using the disclosed methods. Additionally, the agaroid structures formed may take the form of numerous useful shapes, including beads, spheres, microbeads, microparticles, matrices, mats, hollow and non-hollow fibers, as well as other possible shapes and structures with or without an interconnected pore network.

In embodiments in which one or more beneficial agents are incorporated into the agaroid structure, the one or more beneficial agents maty be introduced to the agarose mixture prior to cooling 210 of the agarose mixture. In embodiments in which the one or more beneficial agents are particles, the particles may be entrapped during the precipitation of the agarose from the glycol solution. If the beneficial agents are liquid or dispersed in a fine enough suspension, the beneficial agents may be loaded into the agaroid structure after precipitation at any time prior to use. Beneficial agents may also be somewhat immobilized in the agaroid structure by incorporating the beneficial agents in a gelling or bonding agent or the like, or if possible, gelling or solidifying the beneficial agent itself. Beneficial agents can also be chemically bound (e.g., covalently or ionically) to the agaroid structure, in some embodiments.

Figure 3:
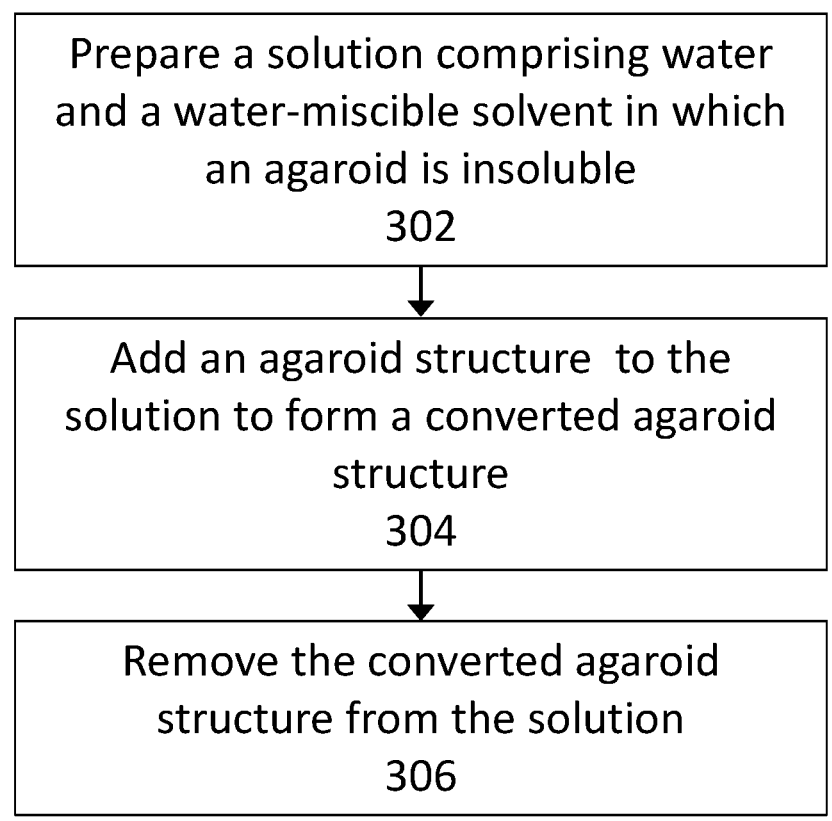
FIG. 3 shows an exemplary method of converting an agaroid structure, in accordance with some embodiments of the subject disclosure.

The resulting agarose/agaroid structure produced according to method 200 may, in some cases, have dissolution properties which render it less suitable for use in or on a mammalian body. Accordingly, the agaroid structure may be further processed, if desired, to impart more suitable dissolution properties (e.g., a dissolution point above 40° C.). An example method that may be used to "convert" the agaroid structure to one with more desirable dissolution properties is detailed in method 300 of FIG. 3. The term "converted agaroid" as used herein, refers to an agaroid material precipitated from a glycol solution and further converted according to, for example, method 300 to have conventional agaroid dissolution properties. In select embodiments, a "converted agaroid" may be identified by having a dissolution point above 40° C. in water. Method 300 includes preparing 302 a solution comprising water and a water-miscible solvent in which an agaroid is insoluble. Example water-miscible solvents in which an agaroid is insoluble include but are not limited to alcohols (e.g., isopropanol) and acetone. The water-miscible solvent in which an agaroid is insoluble is sometimes referred to herein as a "non-solvent." Water and the water-miscible non-solvent may be present in various ratios in the solution. For example, the solution may include water and a water-miscible non-solvent in a weight ratio of 1:5 to 1:1.

Method 300 continues with adding 304 an agaroid structure to the solution to form a converted agaroid structure. Example agaroid structures that may be added 304 to the solution include any agaroid structure 100 previously discussed, including the agaroid structures formed using method 200. In some embodiments, the solution may optionally be cooled prior to or while the agaroid structure is added 304. For full conversion, the agaroid structure remains in the solution until the water content has equilibrated between the solution and the agaroid structure. Method 300 continues with removing 306 the converted agaroid structure from the solution. The converted agaroid structure may be removed 306 from the solution using any suitable separation technique, including centrifuging or filtration.

After formation of the agaroid structure (e.g., by precipitation in a glycol solution according to method 200 and before or after converting the agaroid structure according to method 300, if performed), the agaroid structure may be optionally be processed further, if desired. For example, in some embodiments, the agaroid structure may be cut, chopped, or ground to form smaller, irregularly-shaped particles.

In some embodiments, the agaroid may be cross-linked. Example chemical cross-linking agents that may be used to cross-link the disclosed agaroid structures include but are not limited to: epichlorohydrin, 2,3-dibromopropanol, bis-epoxides, divinyl sulfone, and/or bifunctional isocyanates. In embodiments in which an agaroid structure is chemically cross-linked, the crosslinking agent may be introduced to the agaroid structure after formation in method 200 and before or after conversion according to method 300. A chemically cross-linked agaroid matrix appears to be somewhat more robust than an agaroid matrix that has not been cross-linked. Also, a chemically cross-linked agaroid matrix that has been dried may re-swell to almost 100% original size when exposed to aqueous solutions. In some cases, an agaroid matrix that has been chemically cross-linked linked may collapse upon itself to some degree when dried but may expand decidedly more than an agaroid matrix that has not been cross-linked but has been similarly dried and exposed to an aqueous environment.

In certain embodiments, a converted agaroid (e.g., an agaroid structure formed using methods 200 and 300) may be derivatized after it is formed into a converted agaroid. Similarly, a converted agaroid (e.g., an agaroid structure formed using methods 200 and 300) may be further modified by coupling one or more ligands to the agaroid structure.

In some embodiments, one or more pore-forming agents (alternatively referred to as "porogens" herein) may be used to control the porosity of the resulting agaroid structure. If used, pore-forming agent(s) may be added to the agarose mixture (prior to, during, or after precipitation). Example pore-forming agents that may be used include but are not limited to sodium chloride crystals. Pores or voids can also be formed in an agaroid structure by casting the agaroid structure (e.g., agaroid matrix or other structure) around fibers or other solid shapes that are physically removed (rather than dissolved).

In some embodiments, an agaroid structure may be sintered by, for example, exposing the agaroid structure to conditions in which discrete agaroid structures fuse together. In some example embodiments, agaroid fibers and/or agaroid beads may be sintered together by exposure to conditions that allow the surface of the fibers or agaroid beads or agaroid structure to slightly dissolve and then gel, thereby fusing the structures together resulting in a mat or another type of fused agaroid structure. This can be accomplished, for example, by exposing the agaroid structures to a water and non-solvent water miscible solvent with a somewhat higher water content than that used for method 300.

If desired, one or more beneficial agents may be included in the agaroid structures disclosed herein. In some embodiments, beneficial agents may be added during formation of the agaroid structure, while in other embodiments, beneficial agents may be added to the agaroid structure after its formation. For example, an agaroid matrix may be formed with beneficial agents incorporated within the structure of the agaroid matrix by including one or more beneficial agents before or during the precipitation of the agaroid, thereby forming the agaroid matrix with the beneficial agent entrained within its structure. The agaroid structure with beneficial agent may then be converted according to method 300, as desired.

In other embodiments, beneficial agent(s) may be added to an agaroid matrix after formation. For example, in some embodiments, the porous and sponge-like nature of some agaroid matrices may allow for loading with beneficial solutions, suspensions, or particulates prior to use in the same way a sponge can be loaded by exposure to a liquid containing the desired loading agent. It may prove advantageous to immobilize a beneficial agent in solution, suspension, or particulate form within the pore structure of an agaroid matrix, in some embodiments. This can be accomplished by, for example, including a gelling agent with the beneficial agent(s). In some cases, the beneficial agent itself may be gelled.

In some embodiments, an agaroid structure may be formed within another structure or may be incorporated into another structure after formation to form a composite agaroid structure. For example, in some embodiments, an agaroid matrix may be coupled to flexible or rigid gauze, fabric, open-cell foam, another matrix, or scaffold. In some such embodiments, the hot agarose mixture may be loaded onto the desired coupling structure and the agarose mixture may be allowed to cool to precipitate the agaroid structure. In some cases, the resulting composite agaroid structure may possess additional strength, structure, and/or improved ease of handling.

In some embodiments, an agaroid structure may be loaded with a hydrogel. For example, in some embodiments, an agaroid matrix may be loaded with a hydrogel in liquid form, alone or with additives. In some embodiments, an agaroid matrix may be loaded with a hydrogel by imbibing the hydrogel into the agaroid matrix and subsequently gelling the hydrogel when present inside the agaroid structure. The hydrogel may, in some embodiments, be an agaroid or any other type of hydrogel material.

If desired, one or more beneficial agents may be incorporated into a sintered agaroid structure. If the beneficial agents are particles, they can be entrapped during the sintering process or, if an agaroid matrix is used, the beneficial agents may be entrapped during the forming of the agaroid matrix. If the beneficial agents are liquid or a fine enough solid or suspension, they may be loaded into the sintered agaroid structure or agaroid matrix at any time prior to use. Beneficial agents can also be somewhat immobilized in the sintered agaroid structure by incorporating a gelling or bonding agent or the like or, if possible, gelling or solidifying the beneficial agent itself. Beneficial agents may also be chemically bound to the sintered agaroid structure. In these and other embodiments, pore formers can be incorporated into a sintered agaroid structure during the sintering process to create pores or voids of a desired size and shape, if desired. It will be understood that these exemplary agaroid structures discussed in detail are for illustration purposes and are not intended to limit the scope of the subject disclosure.

Experimental Examples

In a first experimental example, an agaroid structure was produced in the following manner. Propylene glycol (100 mL) was introduced into a 250 mL flask and distilled water (15 mL) was then added to the glycol. 4 g of a commercial grade of agarose (SeaKem® LE agarose, FMC BioProducts, Rockland, Me.) was slowly added to the mixture with stirring. This stirred suspension was heated at 120° C. for 20 minutes until all of the agarose had dissolved. Heating was then discontinued, and the mixture was allowed to cool slowly to room temperature during a two-hour period with gentle to moderate stirring. 20 minutes after cooling was allowed to begin, agarose began to precipitate from the solution. When the temperature of the mixture reached room temperature, it was centrifuged to collect the precipitate. The solid was washed twice with 100 mL of 99% isopropyl alcohol and then was dried in a 55° C. forced air oven. Examination of the solid revealed that it was composed of small, uniformly spherical particles, the majority of which were 1 to 5 microns in diameter. A portion of this solid, purified agarose was placed in stirred water at room temperature. Immediately, the particles began to dissolve in the water, but, before dissolution was complete, a gel began to form on the surface of the particles. Agglomeration of these gel-coated particles followed, preventing further dissolution.

In a second experimental example, an agaroid structure was produced in the following manner. 120 grams of SeaKem® LE agarose, (a product of FMC BioProducts, Rockland, Me., U.S.A.) was suspended in a solution comprising 75 ml water and 3000 ml propylene glycol in a 4 L beaker. The beaker was then placed in the heating mantle, covered, and a Tline mixer inserted into the suspension. The heating mantle was set at about 65% power and the mixer was set at about 45% power. The suspension was heated with mixing until it reached about 110° C., at which point the agarose was entirely dissolved. The mixing was maintained at about 45% and the heating mantle was turned off. The mixing solution was left to cool in the heating mantle overnight. The next morning (after about 18 hours) the solution had cooled to about 30° C. and the agarose had precipitated as 1-5 micron spheroidal microparticles.

In another experimental example, structured agaroid material (e.g., the agaroid microsphere structures produced in experimental examples 1 and 2) were suspended in a mixture containing about 50% of water and 50% of a water-miscible non-solvent for agarose or an agaroid. The non-solvent may be an alcohol, e.g., isopropanol or another type of alcohol or acetone may also be used, as can mixtures of other non-solvents. After standing with or without stirring for a suitable period of time, which can be about 30 minutes or longer, the agaroid structure was converted to having a higher dissolution temperature in water. The converted agaroid structure may optionally be washed with alcohol and dried, or diluted into water, if desired.

Another option for converting the agaroid structure is to take an agaroid structure which has been washed in alcohol or another non-aqueous non-solvent to remove all glycol, re-suspend the agaroid structure in alcohol, and chill to about 5° C. Water chilled to 10° C. or lower may then slowly be added to the chilled agaroid-alcohol suspension with mixing or by diffusion. A possible rate of addition is one volume of water over the course of an hour. For example, ice may be added to the chilled suspension. Progress of the conversion reaction can be conveniently monitored by mixing small samples of the agaroid structure(s) with several volumes of water and observing whether or not the agaroid structure(s) dissolve.

Upon recovery from the solution, it was found that agaroid structures processed in this manner had solubility properties of a conventional agaroid (e.g., a dissolution point of at least 40° C., 50° C., 60° C., 70° C., or 80° C. in water).

Exemplary Methods of Use

The disclosed agaroid structures may be used for any suitable purpose in or on a mammalian body. While some particular examples are described in detail, the disclosed agaroid structures (with or without beneficial agent(s) present) may be used for other additional therapeutic or cosmetic purposes. In some embodiments, the disclosed agaroid structures may be applied to a target site in a subject. Example target sites include tissue, organs, body cavities, bone, meninges, and/or the spinal column. A few exemplary methods of using the disclosed agaroid structures are provided below for illustration purposes. It is to be understood that additional methods and uses for the disclosed agaroid structures may also be possible.

Wound Treatment

The properties of the disclosed agaroid structures, for example, being porous, sponge-like, bio-compatible, biodegradable, and natural may be useful in the field of wound treatment. For example, upon contacting a wound surface or other tissue injury, the disclosed agaroid matrix compositions may provide a form-filling and fitting surface that maintains intimate contact with the wound surface while providing an appropriately moist environment for tissue regeneration. Moreover, the agaroid matrix compositions may also absorb and contain exudates from a wound. The disclosed agaroid matrix compositions may also benefit a wound by not permitting the wound to dry out, thus preventing the bandage or wound dressing from becoming bonded to the wound or the surrounding tissue. Because a moist environment can be maintained, removal of the wound dressing may not damage the wound bed or periwound.

In certain embodiments, the wound or skin injury treated with the disclosed agaroid structures may be a pressure sore, burn, cancer wound, ulcer, surgical site, dermatology wound, traumatic wound, diabetic wound, chronic wound, or acute wound. The term "wound" as used herein refers to all types of tissue injuries, including those inflicted by surgery and trauma, including burns, as well as injuries from chronic medical conditions, such as atherosclerosis, vascular disease, or diabetes. The agaroid matrix compositions described herein may be useful for treatment of all types of wounds, including wounds to internal and external tissues. The disclosed wound dressings are intended to treat the various etiologies of wounds that affect the three layers of the skin—the epidermis, dermis, and subcutaneous layers.

In some particular embodiments, the wound or skin injury may be a site of active bleeding. In such embodiments, the agaroid matrix composition applied may have a hemostatic effect on the bleed site. An agaroid matrix composition used in a hemostatic application may comprise one or more materials that provide a hemostatic function, for instance coagulation-inducing agents. The composition may further include medicinal or therapeutic agents, or pain reducing agents. The coagulation-inducing agent may be selected from thrombin, a snake venom, a platelet activator, a thrombin receptor activating peptide, and a fibrinogen precipitating agent.

In some cases, application of an agaroid matrix or another type of agaroid structure to a wound may reduce the formation or appearance of a scar. Application of an agaroid matrix to a wound may have other therapeutic effects, such as elimination of strong odors, conservation of living fat cells, and/or cessation and reversal of hypergranulation.

The porous sponge-like qualities of the agaroid matrix compositions also make them well-suited to contain beneficial agents that can then be delivered to, and be maintained in contact with, the wound site. These agents can be added to the agaroid matrix at the time of manufacture or can be added just before use. In certain embodiments, the composition used in the treatment of wounds or skin injuries further comprises a therapeutic agent selected from a group consisting of: topical steroids, retinoids, antimicrobial agents, coagulation agents, analgesics, and anesthetics. In select embodiments, the therapeutic agent is selected from antimicrobial agents, coagulation agents, analgesics, and anesthetics.

In some embodiments, an agaroid matrix composition may be incorporated in or deposited on a bandage or compress. In these and other embodiments, the agaroid matrix composition may be, for example, in sheet form, particulate form, beads, or another form. The agaroid matrix may be dried, partially or fully, before application to the wound site, thereby improving its ability to absorb liquids from the wound site. Chemically cross-linking the agaroid matrix before drying may also improve its ability to absorb liquids from the wound site.

Bone Graft Applications

The properties of agaroid matrix compositions described herein are also applicable in the field of bone grafting and bone void filling, and other bone supplement therapies. Bone supplements are used to correct surgical defects that may be caused by trauma, pathological disease, surgical intervention, or other situations in which defects need to be managed, for example, in osseous surgery. Bone supplements also find utility in filling defects or voids in bone material or retaining a bone graft material in a desired position.

The porous, sponge-like, bio-compatible, biodegradable, and natural, properties of the agaroid matrix compositions described herein may render the composition useful to stabilize a bone supplement within its target site, conferring positional stability to the bone supplement and the surrounding tissue. The combined agaroid matrix composition and bone supplement material may be conformable to the surgical site or bone graft site, which is often uneven in shape or depth. Moreover, the components of the agaroid matrix composition may enhance cell proliferation, migration, and adhesion.

In certain aspects, the disclosure provides a method of stabilizing a bone supplement at a bone void or bone graft site, comprising: contacting a bone supplement with a composition comprising an agaroid matrix to form an agaroid matrix-bone supplement mixture; and contacting the bone void or bone graft site with the agaroid matrix-bone supplement mixture. The term "bone supplement" as used herein refers to materials that encourage, enhance, promote, or initiate bone growth, regrowth or grafting. Bone supplement materials are known in the art and may be solids (e.g., powders) or liquids, or a combination thereof. The term "stabilizing" as used herein with reference to bone supplements refers to increasing the retention of the bone supplement in a target site. Retention of a bone supplement may be enhanced by binding a particulate bone supplement into a more cohesive mass, by improving adhesiveness, by providing a matrix for the controlled delivery of the bone supplement, or any combination thereof.

When the bone supplement materials are solids, crushed bone or hydroxyapatite for instance, the bone supplement materials may be incorporated into the agaroid matrix composition at the time of forming the agaroid matrix. That is, they may be introduced into the solution of agaroid dissolved in glycol before or during the precipitation step and thereby be contained within the agaroid matrix as it is formed. This makes for a convenient method of manufacturing, packaging and delivering bone supplements.

If the agaroid matrix compositions with solid bone supplements incorporated within are further dried, they will swell to some extent when exposed to water or bodily fluids. This swelling can prove beneficial if it is desired to completely fill a bone cavity or void or if access to the target site is limited. The water to cause the swelling can be provided by bodily fluids or can be provided from an external source, or a combination thereof. Chemically cross-linking the agaroid matrix-bone supplement prior to drying may further enhance the swelling of the agaroid structure on exposure to water.

If the bone supplements are a liquid or a suspension, they may be loaded into the agaroid matrix, much like loading a sponge. In the case of liquid or suspension bone supplements, the agaroid matrix to be loaded may further contain solid bone supplements. The bone supplement may be further constrained within the agaroid matrix by including a gelling material with the bone supplement within the agaroid matrix and entrapping the bone supplement in the gelling material.

In certain embodiments, the agaroid structure composition described herein may be used in contact with bleeding bone. This condition is created either from trauma or a surgical procedure that may involve drilling, sawing, grinding, or scraping the bone to achieve a bleeding condition. In surgery, the bone is traumatized or surgically cut, exposing blood capillaries, Haversian canals (micro-channels in the bone), periosteum (the protective tissue lining around bone), muscle and other structures in the surgical site. An agaroid matrix composition in combination with bone supplement material may serve as an osteoconductive matrix and may also signal the patient's tissue and cells to initiate growth of new bone (osteoinduction).

An agaroid matrix composition may include one or more additional active and non-active materials that can enhance stabilization of the bone supplement. These materials may be included with the agaroid matrix to reduce discomfort to the patient, increase the radio opacity, improve imaging contrast, introduce medicinal or therapeutic agents to the target site, and/or improve the handling of the composition. Accordingly, in certain embodiments, the composition used in stabilizing a bone supplement at a bone void or bone graft site further comprises an agent selected from the group consisting of: imaging contrast agents, analgesics, and anesthetics.

Dermal Filling and Tissue Bulking

The converted agaroid compositions described herein may also be utilized in applications for filling or bulking tissue. Such applications may be cosmetic or therapeutic. The converted agaroid compositions of the present disclosure are also useful for drug delivery applications. The porous and sponge-like properties of some of the converted agaroid compositions enable them to be applied to a subject (e.g., injected into a subject) in a compliant form. As used herein, the terms "tissue filling" and "tissue bulking" and "filling or bulking soft tissue" include aesthetic smoothing and bulking of the skin, filling scars, filling voids in skin and tissue, or creating masses in tissue or body voids. The term "dermal filling" may also be used to describe any of these processes.

The converted agaroid compositions for dermal filling or tissue bulking can be introduced to the target site in a number of ways including intradermally or subcutaneously, or the composition can be implanted or applied topically. In certain embodiments, the disclosure provides a method of filling or bulking a soft tissue in a subject, the method comprising administering to the soft tissue a composition comprising a converted agaroid. In certain embodiments, the disclosure provides a method of filling or bulking a soft tissue in a subject, the method comprising administering to the soft tissue a composition comprising agaroid microbeads. With attention to the cooling rate of the glycol solution and the type and amount of agitation, the size and shape of the resultant agaroid microbeads can be somewhat controlled. Slow cooling with high agitation can produce spheroid particles in the 1 to 5 micron size range. Fast cooling with high agitation can produce rough high surface area particles in a similar size range. High agitation produces smaller particles while lower agitation produces larger particles. The agaroid micro beads can be small enough to be readily delivered through a small bore needle.

In certain embodiments, the present disclosure provides a method of filling or bulking a soft tissue in a subject, the method comprising administering to the soft tissue a composition comprising agaroid microbeads suspended in a hydrogel. In certain embodiments, the present disclosure provides a method of filling or bulking a soft tissue in a subject, the method comprising administering to the soft tissue a composition comprising a converted agaroid in the form of a thread.

The swelling properties of a dried agaroid matrix composition can prove to be particularly beneficial when it is desired to introduce a relatively large mass into tissue or a body void. An agaroid matrix can be introduced in a dried or partially dried state and will swell when exposed to the water in bodily fluids or water supplied from an external source. The fact that the agaroid matrix is reduced in size during its application can ease the trauma of the application, for example, an agaroid matrix may be inserted through a smaller opening. The agaroid matrix composition can be a single formed piece or smaller particles or beads. Chemically cross-linking the agaroid matrix may enhance the swelling properties of the dried agaroid matrix.

In some embodiments, the agaroid structure further comprises an agent selected from the group consisting of imaging contrast agents, radio-opaque agents, pigmentation agents, anti-pigmentation agents, moisturizing agents, tensioning agents, anti-acne agents, antioxidants, anti-itch agents, anti-cellulite agent, anti-scarring agents, anti-inflammatory agents, analgesics, and anesthetics. These agents can be included with the agaroid matrix in ways previously presented for inclusion of liquids and solids in agaroid matrix.

Drug Delivery

The porous, bio-compatible, biodegradable, and natural properties the agaroid matrix compositions described herein may make them useful in methods for controlled delivery of an active pharmaceutical ingredient on or in a mammalian body. The agaroid matrix can act as a scaffold to contain and protect and deliver a pharmaceutical ingredient by itself or the pharmaceutical ingredient may be further constrained within a gel or gel-like material that is imbibed into or distributed throughout the agaroid matrix. The agaroid matrix-pharmaceutical composition could act as a bolus for short or long-term delivery of a pharmaceutical ingredient within a tissue site or void in a mammalian body. In certain embodiments, the active pharmaceutical ingredient present in the agaroid matrix is selected from topical steroids, retinoids, antimicrobial agents, coagulation agents, analgesics, chemotherapy agents and anesthetics.

Emboli

The sponge-like, bio-compatible, biodegradable, and natural properties the agaroid matrix composition described herein, particularly its ability to swell on exposure to bodily fluids, makes the composition a candidate for creating hemostatic implants and the like. These properties further make the composition a good candidate for conduit occlusion. The conduit may be a naturally-occurring conduit, such as a tube or vessel in the body or may be a conduit that has been introduced in the body such as a medical device or through surgical means.

In certain embodiments, an agaroid matrix composition may be simply inserted in, or applied to, the occlusion site to essentially fill the occlusion site. The conformability of the agaroid matrix may lend itself to fitting into irregular spaces. In certain embodiments, an agaroid matrix may be squeezed like a sponge before being inserted in or applied to the occlusion site and after insertion or application, the agaroid matrix swells to essentially fill the occlusion site. The swelling is enhanced by the presence of bodily fluids, fluids from an external source, or both. Chemical cross-linking of the agaroid matrix may enhance the robustness and re-swelling of the agaroid matrix.

In certain embodiments, the agaroid matrix has its gross volume reduced by partial or essentially complete drying and is inserted in or applied to the occlusion site in this reduced volume state and swells to essentially fill the occlusion site by its contact with bodily fluids, fluids from an external source, or both. The swelling of a dried or partially dried agaroid matrix is enhanced if the agaroid matrix has been chemically cross-linked before it is dried.

The enhanced robustness of chemically cross-linked agaroid matrix makes it particularly beneficial to hemostatic implants and conduit occlusion because in most instances, it is desirable to not have the hemostatic implant or conduit occlusion move out of position or fragment or shed pieces. This robustness also proves to be beneficial in instances where it is desirable to remove the hemostatic implant or conduit occlusion. It can be tethered by enclosing in a compliant mesh type bag or container that has a tether attached, or the tether could be simply tied to the agaroid matrix, or the attachment of the tether could be incorporated into the agaroid matrix when the agaroid matrix is formed. For example, an agaroid matrix may be formed around the tether or the attachment could be more robust by making the end of the tether a porous structure and having the agaroid matrix form in and around that porous structure thereby forming a mechanical bond with the tether. The agaroid matrix could also be chemically bonded to the tether, in some embodiments.

Three-Dimensional Scaffold

The porous, sponge-like, bio-compatible, biodegradable, and natural properties the agaroid matrix composition described herein make it particularly suited to scaffold applications. For example, an agaroid matrix may be used in maxillofacial, orthopedic, oral, and/or plastic surgery procedures as material for tissue augmentation, guided regeneration, and/or tissue engineering approaches.

Developments in tissue engineering approaches frequently revolve around the use of three-dimensional scaffolds to function as the template for cellular activities to repair, rebuild, and regenerate damaged or lost tissues. While there are several biomaterials to select as three-dimensional scaffolds, it is generally agreed that a biomaterial to be used in tissue engineering needs to possess certain material characteristics, such as biocompatibility, suitable surface chemistry, interconnected porosity, desired mechanical properties, and biodegradability. The use of naturally derived polymers as three-dimensional scaffolds has been gaining widespread attention owing to their favorable attributes of biocompatibility, low cost and ease of processing. An agaroid matrix may provide a macroporous structure suitable for cell growth and migration and nutrient transport. An agaroid matrix may be formed with larger than normal voids or pores, if needed, by including sacrificial bodies, pore formers, during the precipitation step of forming the agaroid matrix and removing or dissolving or destroying these bodies after the agaroid matrix has been formed. When a more rigid scaffold is desired, sintered agaroid structures may be employed. These structures are particularly useful when the scaffold requires load bearing properties as in bone and joint regeneration.

Sintered agaroid structures can be formed with larger than normal voids or pores, if needed, by including sacrificial bodies, pore formers, during the sintering step of forming the sintered agaroid structure and removing or dissolving or destroying these bodies after the agaroid matrix has been formed. In certain embodiments in which a more open structure is desirable, agaroid mat properties can be tailored by adjusting fiber size and density in the agaroid mat structure as well as including pore formers during formation of the mat.

Further Exemplary Embodiments

In some aspects, compositions including an agaroid structure made from essentially solid agaroid having a plurality of interconnected pores and one or more beneficial agents are disclosed. In some embodiments, the one or more beneficial agents are dispersed in the pores of the agaroid structure and, in other embodiments, the one or more beneficial agents are dispersed in the essentially solid agaroid. The one or more beneficial agents may be selected from the group consisting of: hyaluronic acid, collagen, and hydroxyapatite, in some embodiments. The agaroid structure may be formed by precipitation from a glycol solution, in some cases. In these and other embodiments, the agaroid structure is converted to be insoluble in water below 40° C. In some embodiments, the one or more beneficial agents are incorporated into the agaroid structure during the precipitation of the agaroid from the glycol solution. The agaroid may be combined with one or more pore forming agents during the precipitation of the agaroid from the glycol solution. If present, the one or more pore forming agents may be insoluble in glycol and soluble in water. The agaroid structure may be in the form of an agaroid matrix, a sintered agaroid, or an agaroid mat and may, in some embodiments, include a chemically crosslinked agaroid, a derivatized agaroid, and/or an agaroid coupled with one or more ligands. In some embodiments, the agaroid structure may be dried.

In another aspect, methods of treating a condition of a mammal are disclosed, which include contacting an area of a mammalian body with a composition having an agaroid structure made from essentially solid agaroid having a plurality of interconnected pores. In these and other embodiments, the composition includes one or more beneficial agents. In some embodiments, the composition further includes a therapeutic agent selected from the group consisting of: antimicrobial agents, coagulation agents, analgesics, and anesthetics. The composition may be applied to a wound or to a skin injury on the mammalian body. In these and other embodiments, the composition is incorporated into or deposited on a bandage or compress. In select embodiments, contacting an area of the mammalian body includes combining the composition with a bone supplement to form an agaroid structure-bone supplement composition and contacting a bone void or bone graft site with the agaroid structure-bone supplement composition. In some embodiments, an active pharmaceutical may be included in the composition. The composition may be implanted into the mammalian body or, in some embodiments, the composition may be used to fill or bulk soft tissue of the mammalian body. In some embodiments, implanting the composition into the mammalian body creates a drug depot or a bolus. In select embodiments, contacting an area of the mammalian body with the composition provides a scaffold for tissue regeneration, wherein the tissue is soft tissue, bone, and/or neural tissue.

In yet another aspect, the present disclosure provides methods of filling or bulking tissue in a mammalian body by implanting a converted agaroid composition into the mammalian body. In some embodiments, the composition includes converted agaroid microbeads and/or converted agaroid particles. In select embodiments, the composition may further include a carrier composition. The carrier composition may be a liquid or a gel, in some embodiments.

The invention claimed is:

1. A composition comprising a solid agaroid precipitate having a plurality of interconnected pores and one or more beneficial agents selected from the group consisting of: hyaluronic acid, collagen, and hydroxyapatite, wherein the solid agaroid precipitate is not a hydrogel and has a dissolution point above 40° C. in water, and wherein the one or more beneficial agents are dispersed and immobilized in the pores of the solid agaroid precipitate by a gelling or bonding agent.

2. The composition of claim 1, wherein the solid agaroid precipitate comprises a chemically crosslinked agaroid.

3. The composition of claim 1, wherein the solid agaroid precipitate comprises an agaroid coupled with one or more ligands.

4. The composition of claim 1, wherein the solid agaroid precipitate is dried.

5. A method of treating a wound of a mammal, the method comprising contacting an area of a mammalian body with the of claim 1.

6. The method of claim 5, wherein the composition further comprises a therapeutic agent selected from the group consisting of: antimicrobial agents, coagulation agents, analgesics, and anesthetics.

7. The method of claim 5, wherein the composition is incorporated into or deposited on a bandage or compress.

8. The method of claim 5 wherein contacting an area of the mammalian body includes:
    combining the composition with a bone supplement to form a solid agaroid precipitate-bone supplement composition; and contacting a bone void or bone graft site with the solid agaroid precipitate-bone supplement composition.

9. The method of claim 5, wherein contacting an area of the mammalian body comprises implanting the composition into the mammalian body.

10. The method of claim 9, wherein contacting an area of the mammalian body comprises filling or bulking soft tissue of the mammalian body with the composition.

11. The method of claim 5, wherein contacting an area of the mammalian body with the composition provides a scaffold for tissue regeneration and the tissue is soft tissue, bone, or neural tissue.

* * * * *